United States Patent [19]
Holmes et al.

[11] Patent Number: 6,019,721
[45] Date of Patent: Feb. 1, 2000

[54] CAMERA WITH IMPROVED FOCUS MECHANISM

[75] Inventors: David P. Holmes, Santa Barbara, Calif.; Douglas A. Golay, Coon Rapids, Iowa

[73] Assignee: Integra Medical, Camarillo, Calif.

[21] Appl. No.: 09/094,234

[22] Filed: Jun. 9, 1998

[51] Int. Cl.$^7$ .................................................. A61B 1/002
[52] U.S. Cl. .................... 600/167; 600/109; 600/131; 600/168; 600/182; 433/29
[58] Field of Search ..................................... 600/109, 131, 600/167, 168, 170, 182, 200; 433/29

[56] References Cited

U.S. PATENT DOCUMENTS

| | | | |
|---|---|---|---|
| 4,182,547 | 1/1980 | Siegmund | 385/117 |
| 4,558,691 | 12/1985 | Okada | 600/117 |
| 4,765,313 | 8/1988 | Kumakura | 600/167 |
| 4,901,144 | 2/1990 | English et al. | 348/69 |
| 4,905,082 | 2/1990 | Nishigaki et al. | 348/73 |
| 4,969,450 | 11/1990 | Chinnock et al. | 600/109 |
| 5,051,824 | 9/1991 | Nishigaki | 348/68 |
| 5,191,879 | 3/1993 | Krauter | 600/109 |
| 5,278,642 | 1/1994 | Danna et al. | 348/70 |
| 5,290,168 | 3/1994 | Cooper et al. | 433/29 |
| 5,408,992 | 4/1995 | Hamlin et al. | 600/169 |
| 5,487,661 | 1/1996 | Peithman | 433/29 |
| 5,527,261 | 6/1996 | Monroe et al. | 600/109 |
| 5,528,432 | 6/1996 | Donahoo | 359/894 |
| 5,575,757 | 11/1996 | Kennedy et al. | 600/167 |
| 5,702,349 | 12/1997 | Morizumi | 600/131 |
| 5,737,013 | 4/1998 | Williams et al. | 348/66 |
| 5,797,836 | 8/1998 | Lucey et al. | 600/109 |
| 5,836,762 | 11/1998 | Peithman | 433/29 |
| 5,879,289 | 3/1999 | Yarush et al. | 600/179 |

*Primary Examiner*—Linda C. M. Dvorak
*Assistant Examiner*—Brad C. Blaise
*Attorney, Agent, or Firm*—Blakely, Sokoloff, Taylor & Zafman

[57] ABSTRACT

A focus mechanism having an actuator positioned near the rear of a handheld piece and that allows a lens element to be moved with respect to a stationary image sensor to achieve a range of focus. When implemented as a manual focusing feature of an intraoral dental camera or handpiece, the focus mechanism allows greater control of focus as the user's hand that grasps the actuator (e.g., ring) is not in close proximity to the distal end of the camera which is inserted into the patient's mouth. Maintaining the image sensor stationary also helps increase system reliability. In a particular embodiment, a variable profile cam allows high precision focus with the camera inside the patient's mouth, while still allowing enough focus travel for capturing a head shot or an image of the patient's smile or face when the camera is moved outside the patient's mouth.

17 Claims, 3 Drawing Sheets

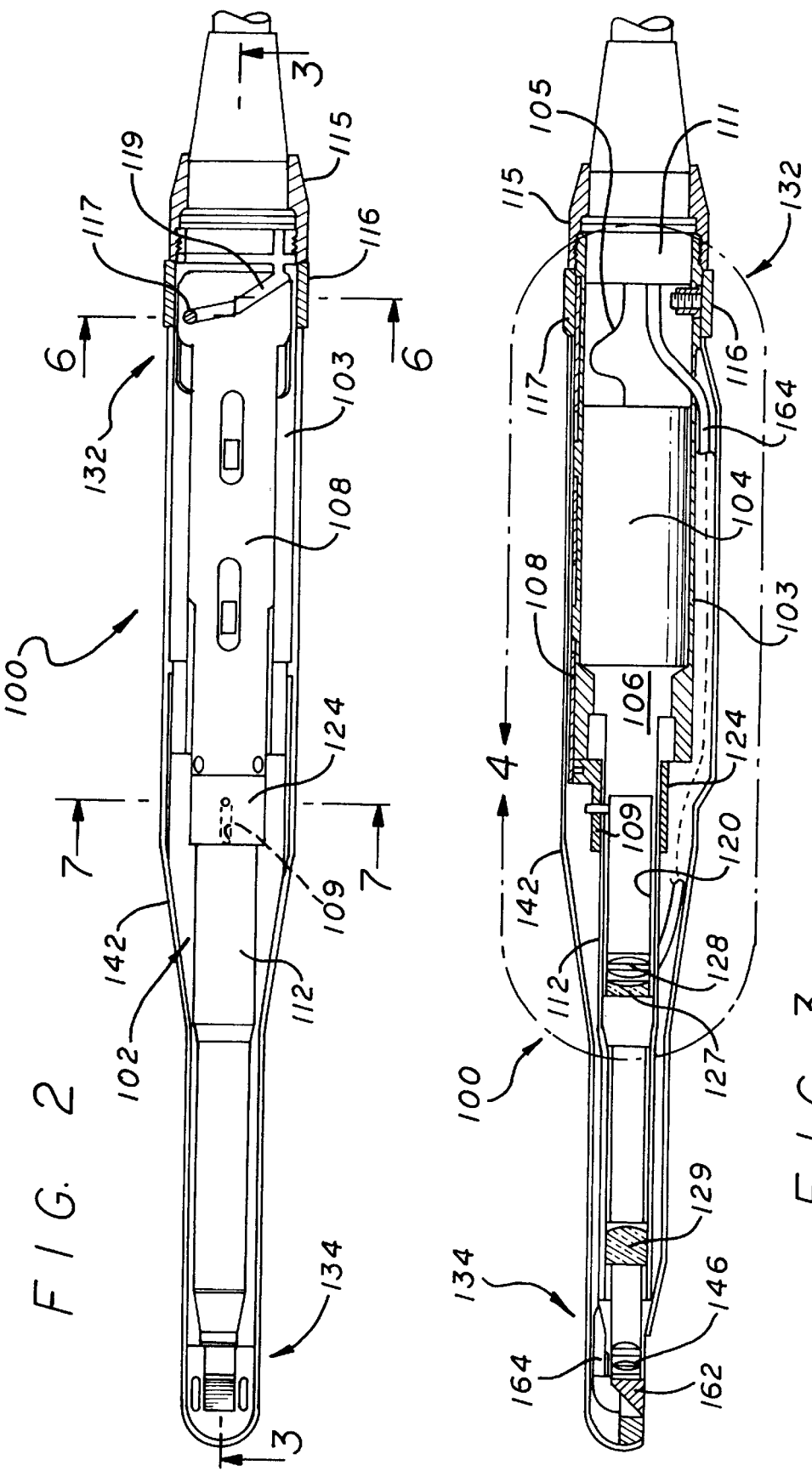

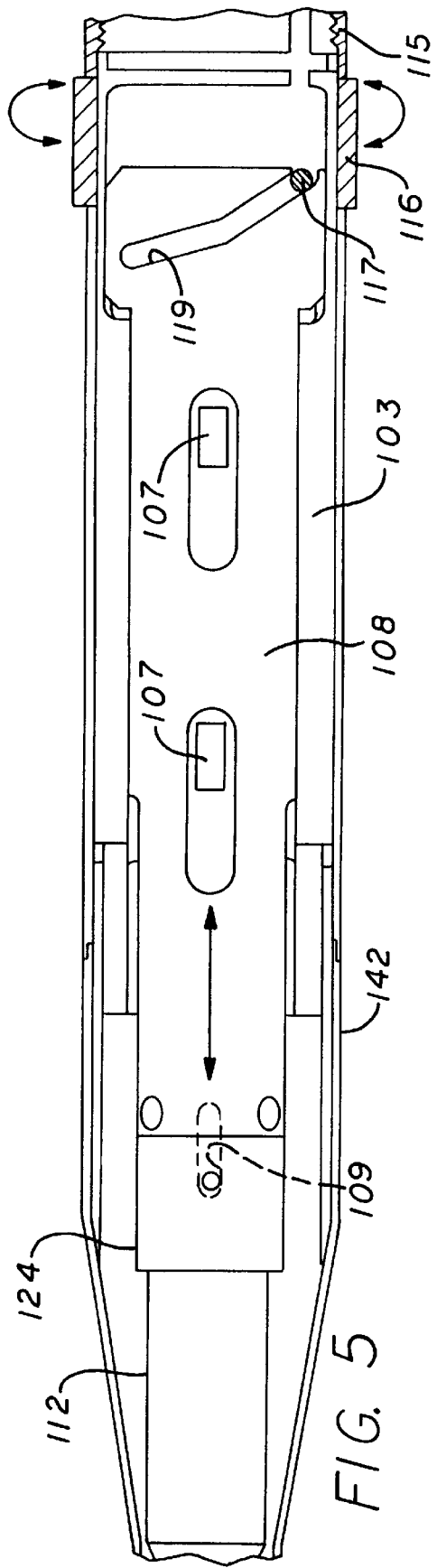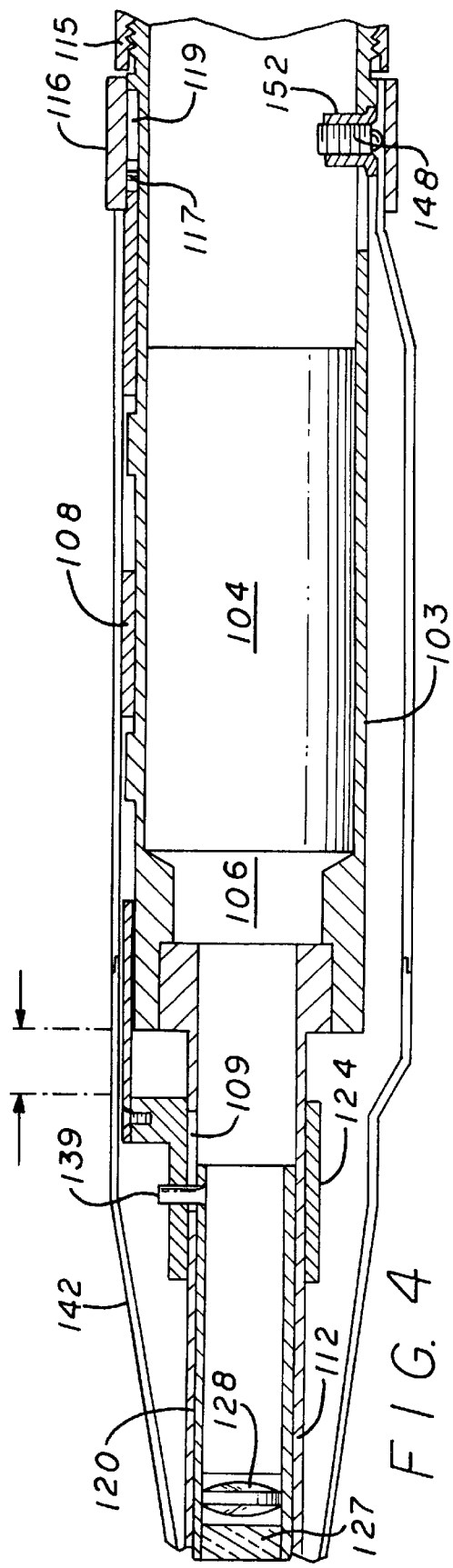

CAMERA WITH IMPROVED FOCUS MECHANISM

BACKGROUND INFORMATION

1. Field of the Invention

This invention is generally related to electronic cameras and more specifically to focusing mechanisms in electronic handheld cameras configured with intraoral imaging optics.

2. Description of Related Art

Electronic handheld cameras configured with intraoral imaging optics ("intraoral cameras") are used for capturing images of the inside of a patient's mouth. The camera typically has an elongated body that contains an image sensor and optics. The optics and the sensor are designed for capturing images of the inside of the mouth when the distal end of the camera is inserted into the patient's mouth. Wires carrying electronic signals typically connect the image sensor to the proximal end of the camera where a communication interface is provided to an image processing system or monitor that allows manipulation and display of the images.

Several types of focus mechanisms for the intraoral camera have been developed. One type has a rotatable dial located at approximately half-way between the proximal and distal ends. Focusing is accomplished by rotating the dial which translates into linear motion of a focusing lens with respect to a stationary image sensor. The focusing lens is positioned between the image sensor and optical elements near the distal end. Locating the dial in the middle of the camera, however, places the user's hand too close to the patient's mouth when focusing.

An alternative technique for an intraoral camera places the focus dial farther away from the distal end, at the proximal end of the camera. In that case, rotation of the dial moves the image sensor relative to the optics to achieve focus. Although in that case the dial is conveniently located far from the distal end of the camera which is inserted into the patient's mouth, long term use by repeated focusing might result in the failure of the wire connection between the image sensor and the proximal end of the camera.

Therefore, a novel intraoral camera is needed which permits a more reliable electrical connection to the image sensor while at the same time allowing the user to focus with her hand away from the patient's mouth and preferably at the rear of the camera.

SUMMARY

Accordingly, one embodiment of the invention is directed at a camera handpiece having a body with a proximal end and a distal end, and a cavity formed therein. The distal end has an opening for light to enter the cavity. An image sensor is stationary and located inside the cavity to receive the light. An actuator is coupled to the body and positioned near the proximal end. A drive is coupled to the actuator. A lens element is coupled to the drive and movably disposed in the cavity for focusing the light onto the image sensor in response to movement of the actuator.

BRIEF DESCRIPTION OF THE DRAWINGS

FIG. 2 is a view of the camera taken generally on line 2—2 of FIG. 1, according to another embodiment of the invention.

FIG. 3 is a sectional view of the camera taken generally on line 3—3 of FIG. 2.

FIG. 4 is an enlarged sectional view of the camera showing a collar and lens carrier according to another embodiment of the invention.

FIG. 5 is a top plan view of an embodiment of the camera.

DETAILED DESCRIPTION

As briefly summarized above, the invention provides for a focus mechanism that can be actuated at the proximal end of a handheld camera, with the image sensor being stationary and the lens element being movable to achieve focus. The invention is particularly useful with intraoral (dental) cameras having a handpiece whose distal end is inserted into a patient's mouth.

Figure 1:
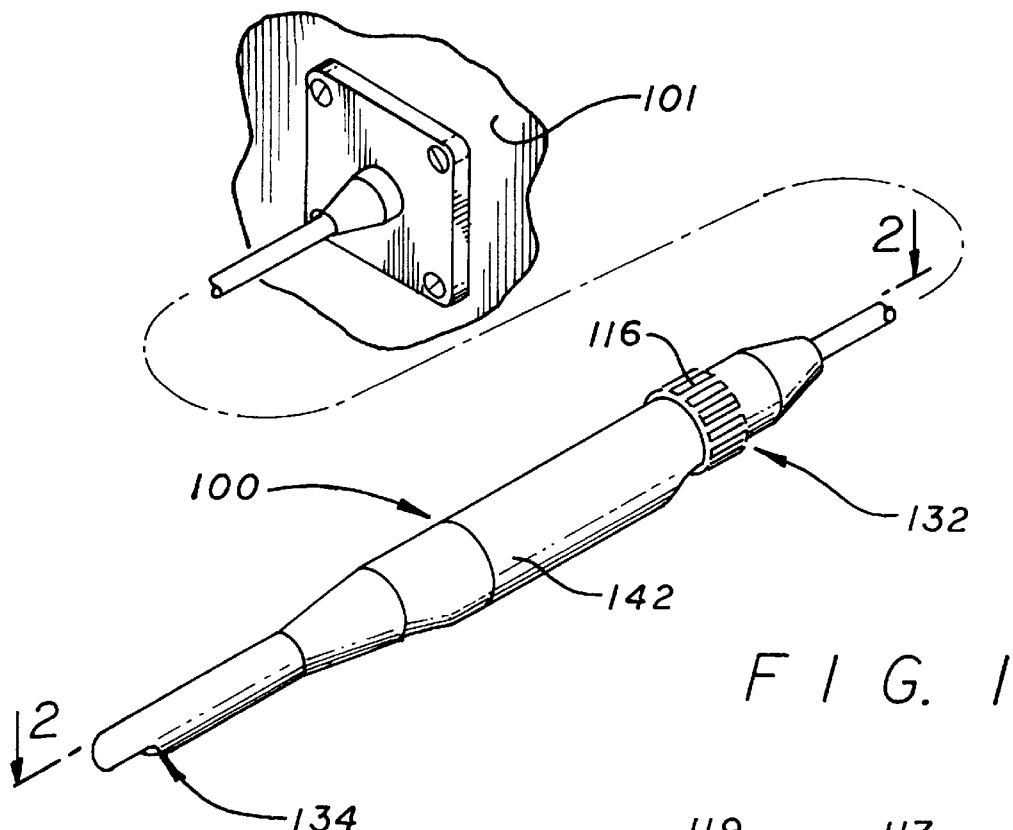
FIG. 1 is a perspective view of a camera according to an embodiment of the invention.

FIG. 1 illustrates an embodiment of the invention as a camera 100. The camera has a distal end 134 and proximal end 132 being at opposite ends of an outer casing 142. An actuator used for focusing comprising a ring 116 in this embodiment is provided near the proximal end. FIGS. 2 and 3 show a perspective view and a side sectional view of an embodiment of the camera 100. The camera 100 has a body 102 with a cavity 106 formed therein between the distal end 134 and the proximal end 132. An image sensor 104 is fixed in a stationary manner to the body 102. The image sensor, in one embodiment, is particularly suitable for intraoral imaging, such as one based on charge coupled device (CCD) technology. A cable assembly 105 electrically connects the sensor 104 to an interface at the proximal end 132. The interface is used to communicate with an image processing system 101.

The camera 100 may be equipped with a light source near the distal end 134 to illuminate the subject during imaging. In the particular embodiment of FIG. 3, this light source is obtained using an optical fiber 164 used as a light transmission medium to channel light generated beyond the camera 100 to the distal end of the camera and out onto the subject (not shown). The cavity 106 extends to the distal end 134 of the camera forming an opening for light reflected from a subject to enter the body 102. Light reflected from the subject enters through the prism 162 and is further guided onto an optional relay lens 129 and through to a lens element 128.

The lens element 128 is movably disposed in the cavity 106 for focusing light onto the image sensor 104. The lens element 128 is coupled to a drive 108. In one embodiment, the drive 108 forms part of a cam together with the ring 116. The ring 116 is fixed near the proximal end 132 in a direction parallel to a longitudinal axis of the body 102, between a portion of the outer casing 142 and a dress nut 115. Rotation of the ring 116 around the axis translates into linear motion of the drive 108 by way of a pin 117 engaging and pushing against a cam slot 119 in the drive 108. Focusing is thus achieved by moving the actuator, e.g., rotating the ring, which causes linear movement of the lens element 128 with respect to the stationary image sensor 104. Alternatives to the rotatable ring 116 may be a rotatable wheel or other suitable actuator such as a motor driven assembly. An alternative to the rotatable mechanism forming a cam with the drive 108 may be a lever having linear movement and featuring some gain such that the lever has greater travel than the drive.

In the particular embodiments illustrated herein, the body 102 is made of several sections that are attached together during assembly of the camera 100. A head body 103 houses the image sensor 104, cable assembly 105, and the interface 107. A cylindrical lens tube 112 is connected to the head body 103, where the cavity 106 extends into both the head body 103 and the lens tube 112. A carrier 120 is movably disposed in the lens tube 112, the carrier holding the lens element 128. The carrier 120 is sized to slidably fit inside the lens tube 112. The carrier 120 is coupled to the drive 108 through a longitudinal slot 109 in the lens tube 112.

Figure 7:
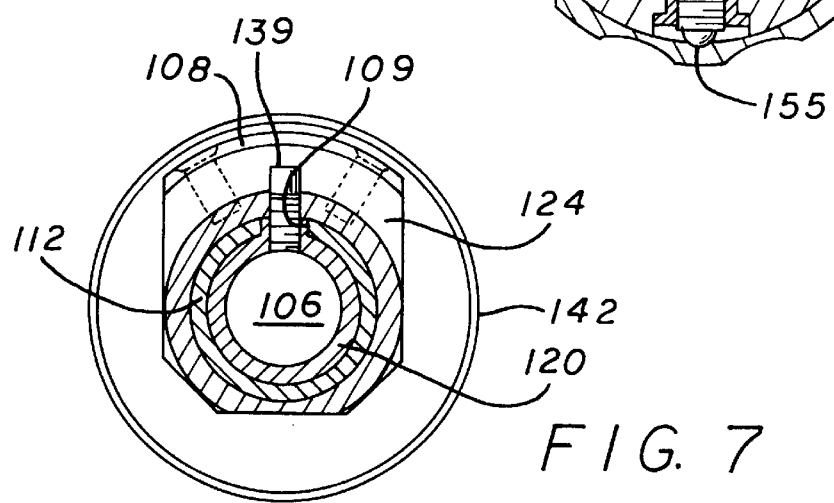
FIG. 7 is a sectional view taken generally on line 7—7 of FIG. 2.

Referring now to FIGS. 4 and 7, the coupling between the carrier 120 and the drive 108 may be accomplished by means of a collar 124 that is movably engaging an outer surface of the lens tube 112 and is coupled to the drive 108. The collar 124 is coupled to the carrier 120 by means of a fastener 139 through the slot 109 in the lens tube 112. In one embodiment, the fastener may be a set screw. The set screw has a top portion which is threaded into a corresponding hole in the collar 124 while the collar is aligned with the slot 109 and the carrier 120 inside the lens tube. The bottom portion of the set screw is not threaded and engages a corresponding hole in the carrier 120. Means other than the above for coupling the collar lens element 128 to the drive may be used such as a direct pin from the drive to either the carrier 120 or the lens element 128 itself.

FIG. 7 illustrates a sectional view taken generally on line 7—7 of FIG. 2. The cavity 106 can be seen inside the cylindrical lens tube 112 having the slot 109 and containing the carrier 120. The collar 124 is shown with the fastener 139 coupling the carrier 120 to the collar 124. The collar 124 is in turn coupled to the drive 108 via two screws. The drive 108 in this embodiment is a thin arcuate piece. However, alternatives may be a flat piece that slides against a corresponding flat section of the head body 103.

The camera 100 may house one of a combination of different optics. In one embodiment, such optics can be configured for intraoral imaging. As shown in FIG. 3, the optics may include a relay lens 129 that works in conjunction with the movable lens elements 127 and 128. Alternatively, the relay lens may be eliminated in favor of a direct optical system. The right angle prism 162 and a micro lens 146 may be attached to the distal 134 to further enhance performance for intraoral imaging.

In the embodiment of the invention illustrated in FIGS. 4 and 5, the drive 108 is a thin piece that can slide against a corresponding surface of the body 102, and in particular the head body 103. The drive 108 can be slidably moved in a direction parallel to the common longitudinal axis of the lens tube 112 and the head body 103, and may be guided by posts 107 on the head body 103. The drive has a cam slot 109 that is engaged by a pin 117 connected to the inside surface of the ring 116. In this embodiment, the drive 108 and the ring 116 are located such that the drive 108 extends past the image sensor 104 before being coupled to the collar 124. The image sensor 104 is fixed at a stationary location between the ring 116 and the movable lens element 128.

In the embodiments of the invention described above, the cam slot 119 may have either a fixed profile or variable profile as shown in FIGS. 2 and 5. The variable profile allows two ratios of rotational movement of the ring 116 to linear movement of the drive 108. For instance, the variable profile of FIG. 5 can be used to obtain three focus regions, one for capturing fine detail of the subject (e.g., detail of intraoral tissue), one for normal image detail corresponding to the pin 117 located at the boundary between the different profiles (e.g., teeth and gums), and one for capturing images of subjects that are farther away (e.g., the mouth and face of a patient taken with the distal end 134 of the camera 100 outside of the patient's mouth).

Figure 6:
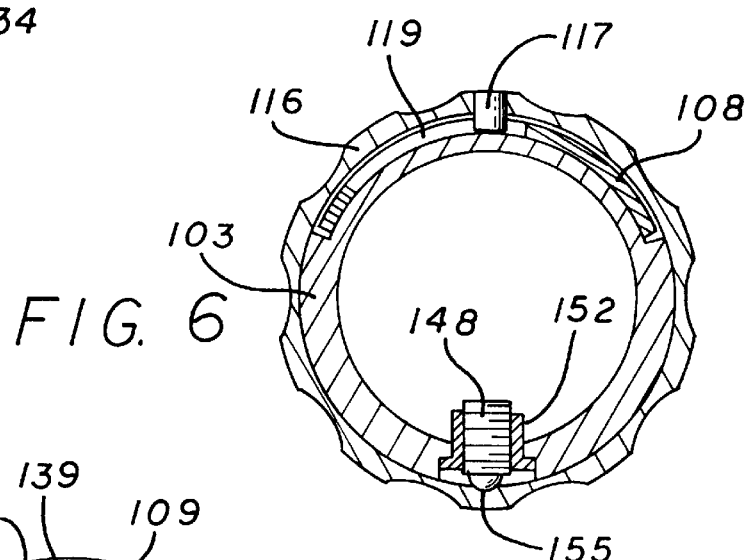
FIG. 6 is a sectional view taken generally on line 6—6 of FIG. 2.

The variable profile may be selected to allow the same amount of rotational movement on either side of a center of position of the ring 116 to correspond to different optical distances covered by the moving lens element 128. A detent mechanism such as the one illustrated in FIG. 6 can also be provided. FIG. 6 shows a sectional view taken generally on line 6—6 of FIG. 2, and shows a spring loaded ball bearing 148 provided in the head body 103. A corresponding detent slot 155 in the ring 116 is designed to receive the ball of the bearing 148 at the center position of the ring 116, giving the user a tactile sense of a mid-range focus when the pin 117 is located in the boundary between the different profiles of the cam slot 119.

A wide range of different materials may be used for the different components of the camera 100 described above. For instance, the head body 103 can be made of an engineering plastic such as ERTALYTE or a fiberglass filled nylon material. The drive 108 may be made of stainless steel, or other high strength material in view of the relatively thin cross-section of the drive. The lens tube 112, collar 124, and carrier 120 may be made of aluminum, and sized so that the collar 124 slides easily against the outer surface of the lens tube 112 and the carrier 120 slides easily against the inside surface of the lens tube 112.

To summarize, the invention has been illustrated by several embodiments of a handheld camera equipped with a focus actuator conveniently located near its proximal end. In one embodiment, a cam mechanism translates rotational movement of a ring around an image sensor into linear movement of one or more lens elements in front of the image sensor, the image sensor being stationary. Keeping the image sensor stationary helps increase system reliability due to less stress being placed on the electrical connections to the image sensor.

The embodiments of the invention described, are of course, subject to some variations in structure or use. For example, although some of the figures illustrate the head body 103 being cylindrical in cross section, other shapes may be used that still have the cavity 106 and support the drive 108. Also, in the intraoral embodiment of the camera, the position of the ring near the proximal end of the camera allows the user to easily focus the camera, where the camera may be held by one hand of a user and focused with the user's other hand. Alternatively, the camera may be held and focused with the same hand. In both instances, the focusing hand is advantageously kept away from the patient's mouth when the distal end of the camera is inserted into the patient's mouth. In general, the embodiments described above are merely designed to illustrate the invention and should not be construed to limit the scope of the invention which is determined by the claims and their legal equivalents.

What is claimed is:

1. A camera comprising:
   a body having a proximal end, a distal end, and a cavity, the distal end having an opening for light to enter the cavity, the body having a lens portion with a slot therein;
   image sensor mounted in a fixed position inside the cavity;
   actuator drive coupled to the actuator coupled to the body and positioned near the proximal end;
   collar movably engaging an outside surface of the lens portion of the body and coupled to the drive;

carrier movably disposed in the lens portion of the body and coupled to the collar through the slot in the lens portion; and lens element held by the carrier for focusing light onto the image sensor in response to movement of the actuator.

2. The camera of claim 1 wherein the actuator comprises a ring rotatably coupled to the body, and wherein the drive and the ring form a cam for translating rotational movement of the ring into linear movement of the drive.

3. The camera of claim 2 wherein the drive has a cam slot engaged by a pin connected to the ring.

4. The camera of claim 1 further comprising:

optics disposed near the opening in the distal end, the optics and the lens element being configured for intraoral imaging.

5. The camera of claim 1 wherein the image sensor is located between the actuator and the lens element.

6. The camera of claim 1 wherein the lens portion of the body is cylindrical.

7. A handheld article comprising:

a head body having a proximal end and a cavity, the head body having a cylindrical outside surface;

a cylindrical lens tube coupled to the head body and having a distal end, the distal end having an opening for light to enter the cavity through the tube;

image sensor being stationary inside the cavity;

actuator coupled to the head body near the proximal end;

drive coupled to the actuator and having an arcuate cross-section mated to the outside surface of the head body; and lens element coupled to the drive and movably disposed in the tube for focusing the light onto the image sensor in response to movement of the actuator.

8. The handheld article of claim 7 wherein the actuator comprises a ring being fixed in a direction parallel to a longitudinal axis of the head body and being rotatable about the axis.

9. The handheld article of claim 7 wherein the lens element is configured for intraoral imaging.

10. A camera comprising:

a body having a proximal end, a distal end, and a cavity, the distal end having an opening for light to enter the cavity;

image sensor mounted in a fixed position inside the cavity;

actuator having a ring rotatably coupled to the body and positioned near the proximal end, the ring having a pin connected thereto;

drive having a cam slot engaged by the pin for translating rotational movement of the ring into linear movement of the drive; and lens element coupled to the drive and movably disposed in the cavity for focusing light onto the image sensor in response to movement of the actuator.

11. The camera of claim 10 wherein the cam slot has a variable profile shaped to provide at least two different ratios of rotational movement of the ring to linear movement of the drive.

12. The camera of claim 11 wherein the cam slot is shaped to provide different focus travel of the lens element on either side of a center position, for the same amount of rotational movement of the ring in opposite directions.

13. The camera of claim 12 further comprising:

detent for providing a tactile sense of a mid-range focus.

14. The camera of claim 10 wherein the body comprises a cylindrical lens tube portion in which a carrier is movably disposed, the carrier holding the lens element and coupled to the drive through a slot in the lens tube.

15. The camera of claim 14 further comprising:

collar movably engaging an outside surface of the lens tube portion and coupled to the drive, the collar being coupled to the carrier through the slot in the lens tube.

16. The camera of claim 10 further comprising:

optics disposed near the opening in the distal end, the optics and the lens element being configured for intraoral imaging.

17. The camera of claim 10 wherein the image sensor is located between the actuator and the lens element.

* * * * *